United States Patent [19]
Skladnev et al.

[11] Patent Number: 5,941,834
[45] Date of Patent: Aug. 24, 1999

[54] SHEATH FOR A SIDE VIEW PROBE

[75] Inventors: Victor N. Skladnev, Vauclude; Richard L. Thompson, Killarney Heights, both of Australia; Irwin Wunderman, Mountain View, Calif.

[73] Assignee: Polartechnics Limited, Sydney, Australia

[21] Appl. No.: 08/818,921

[22] Filed: Mar. 17, 1997

[51] Int. Cl.⁶ .................................................. A61B 5/103
[52] U.S. Cl. ............................................................ 600/587
[58] Field of Search .................................. 600/590, 593; 607/133, 138

[56] References Cited

U.S. PATENT DOCUMENTS

| | | | |
|---|---|---|---|
| 3,480,003 | 11/1969 | Crites | 600/593 |
| 3,647,299 | 3/1972 | Lavallee | 356/41 |
| 3,910,701 | 10/1975 | Henderson et al. | 356/39 |
| 3,994,590 | 11/1976 | Di Martini et al. | 356/178 |
| 4,587,421 | 5/1986 | Robertson | 250/239 |
| 4,873,996 | 10/1989 | Maurer | 607/138 |
| 4,942,877 | 7/1990 | Sakai et al. | 128/633 |
| 5,036,853 | 8/1991 | Jeffcoat et al. | 128/634 |
| 5,411,024 | 5/1995 | Thomas et al. | 128/634 |
| 5,427,093 | 6/1995 | Ogawa et al. | 128/633 |
| 5,520,177 | 5/1996 | Ogawa et al. . | |

OTHER PUBLICATIONS

Mendelson, Ph.D. et al., Design and Evaluation of a New Reflectance Pulse Oximeter Sensor, Medical Instrument, vol. 11, No. 4, pp. 187–173, 1988.

Neuman, M.R., In Medical Instrumentation: Application and Design, pp. 265–266, Webster, J.G. (ed) 2nd Ed. Boston: Houghton Miffliin, 1992.

*Primary Examiner*—Cary O'Connor
*Assistant Examiner*—Pamela Wingood
*Attorney, Agent, or Firm*—Gottlieb, Rackman & Reisman, P.C.

[57] ABSTRACT

A sheath for a side view probe having at least two complete hybrid optical and electrode systems on opposite faces of a cylinder, in order to obviate the need to manipulate the probe through more than a half revolution during examination by the doctor. The sheath covers the probe but allows both electrical and optical measurements to be made by the underlying probe on the same areas of tissue. The invention uses the hoop tension in the sheath to apply the needed spring force to maintain electrode contact. In addition, the probe and its sheath are shaped to ensure both good electrical contact and reliable optical pathways. A built-in means of calibration of the sheath enclosed probe is achieved by attaching to the outside of the tip of the sheath a tube or blocks of a turbid material such as a polymer of controlled composition. The tube or blocks of turbid material are removed prior to using the probe on a patient.

7 Claims, 4 Drawing Sheets

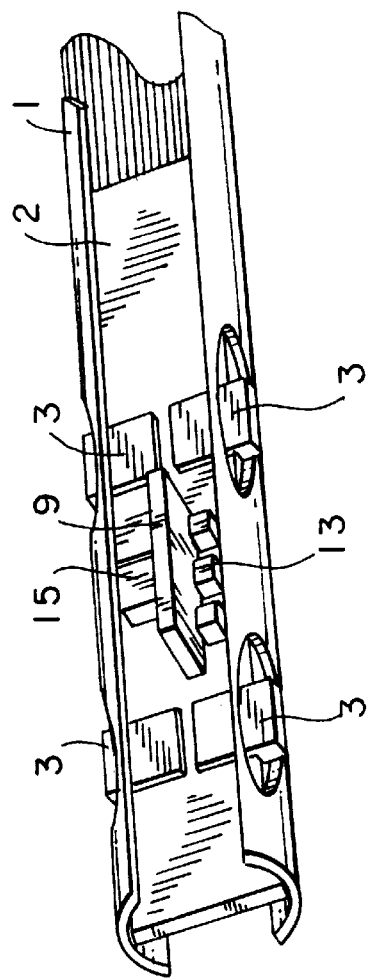
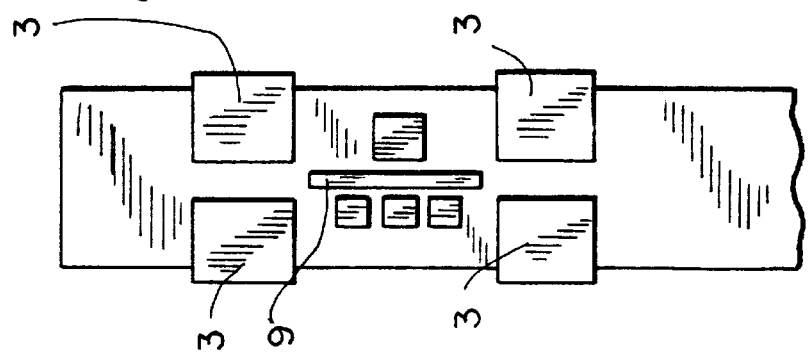
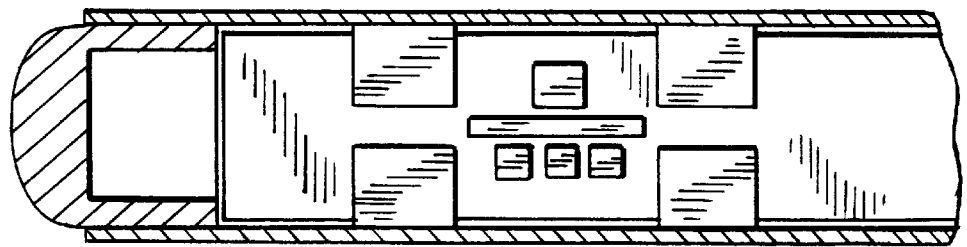

SHEATH FOR A SIDE VIEW PROBE

FIELD OF THE INVENTION

This invention is a sheath intended for use with the probe for identifying different tissue types within body canals such as the endocervical canal. The tissues identified are those displaying modifications involving pre-cancerous and cancerous stages, diseased or traumatized tissue, and those in a transitional stage. Such a probe performs both optical and electrical measurements while it is scanned over the surface of the endocervix or other canal and from these measurements makes a diagnosis of the health of the tissue.

BACKGROUND OF THE INVENTION

The medical profession often needs to have an objective assessment of the health of the tissue of a patient. The patient may have suffered tissue damage as a result of accidental or deliberate trauma as for example during a surgical operation. The patient may also be suffering some other more persistent irritation as a result, for example, of being confined to bed which can lead to bed sores. It is valuable for a medical practitioner to be able to tell in advance the type of treatment that would benefit the patient.

It is well known, for example, that early detection of tissues displaying pre-cancer or cancer modifications is important for successful medical treatment. We have already disclosed an apparatus and method for carrying out this detection in patent application Ser. No. 08/332,830, assigned to the same assignee as the current invention, the disclosure of which is incorporated by reference herein.

Between uses probes can be disinfected by soaking in a suitable solution. For many patients this procedure is not acceptable. They require that the probe has not previously been used on other patients for fear of cross-contamination and infection. This requirement can be achieved by equipping the probe with a disposable, sterile sheath. Such an assembly must ensure that no part of the probe which is used on a patient could have come in contact with a previous patient. Sheaths that have been designed for other types of probes lack features that would make them suitable for use on a probe that performs both optical and electrical measurements while it is scanned over the surface of the cervix. For example ultrasonic probe sheaths would not be suitable. In particular they do not have provision to make simultaneous optical and electrical measurements. The particular difficulties that have been overcome by this invention arise from the fact that the both electrical and optical measurements are to be performed on the same area of tissue. It is therefore not feasible to install a simple sheath such as a condom over the tip of the probe. Such a sheath may, for example, enable some optical measurements to be made but would prevent electrical contact being made with the tissue with the optically transparent cover in place.

It is becoming common practice to equip probes with sheaths for the reasons given above. Sheaths that have been designed for other types of probes lack features that would make them suitable for use on probes that are able to make simultaneous optical and electrical measurements. Previous probes have been either designed for optical or electrical measurements but not for both simultaneously on the same area of tissue.

SUMMARY OF THE INVENTION

The present invention is concerned with providing a sheath for an endocervical probe. Such a probe is disclosed in a copending application filed this same date and entitled "Apparatus For Tissue Type Recognition Within A Body Canal", which is incorporated herein by reference. As explained in that application, in a preferred embodiment of the endocervical probe, there are two complete hybrid optical and electrode systems on opposite faces of a cylinder, in order to obviate the need to manipulate the probe through more than a half revolution during examination by the doctor. This device overcomes the inability to make optical measurements of this type using fibers, because of the infeasibility of bending optical fibers through a right angle to make measurements accurately in a radial direction out of the probe.

In some applications the probe will typically be held in one hand while the other is used to hold a speculum. This means that the probe cannot be passed from hand to hand during the probing operation. As a consequence rotation of the probe during the examination through more than 180 degrees is difficult. Since a full circle of examination is necessary during probing, it has been arranged for the endocervical probe to scan in two opposing directions at once. This enables a full scan of the bore of the canal to be performed with only a 180 degree rotation of the probe. Additional sensing systems could in theory be mounted around the barrel of the probe and thereby reduce the amount of rotation needed but in practice this may not be realistic.

The configuration of the endocervical probe presents particular problems in the design of a sheath that covers each of the active probe areas without inhibiting the function of the probe.

The particular difficulties that have been overcome by this invention arise from the fact that the measurements to be performed are both electrical and optical on the same area of tissue. It is therefore not feasible to install a simple sheath over the tip of the probe. Such a sheath may, for example, enable optical measurements to be made but would prevent electrical contact being made with the tissue with the optically transparent cover in place. This difficulty is overcome in the present invention by incorporating electrodes in the body of the sheath.

The electrodes, for example, have to be positioned relative to the optical window in such a way as to ensure that sealing is not compromised by the presence of the electrodes. The electrodes have to be close by to ensure that both the optical and electrical measurements are made on the same area of tissue.

A further difficulty that is overcome by this invention is the requirement that electrical contact is made in a reliable manner between the internal probe electrical connections and the electrodes in the sheath. The problem is complicated in an endocervical probe where multiple elements radiate outwards from the walls of the probe. Any failure of these connections during probing could lead to false readings with serious consequences to the patient. Because the optical window has to be relatively thin and the electrodes are nearby, pressure exerted by a spring contact on the electrode has the potential to break the seal between the electrode and the window. The special configuration used in this invention avoids this danger by using the hoop tension in the sheath to apply the needed spring force to the electrode contact. In addition, the probe and its sheath are shaped to ensure both good electrical contact and reliable optical pathways.

In addition, we have developed a built-in means of calibration of the sheath-enclosed probe. This is achieved by attaching to the outside of the tip of the sheath a tube or blocks of a turbid material such as a polymer of controlled composition. This material acts in the manner of the tissue to be measured in that it backscatters the light from the probe tip to a controlled degree. This enables the probe's computer to check the overall performance of the optical system thereby verifying that the probe and its sheath are performing optically according to specifications and that the sheath has been correctly fitted. The tube or blocks of turbid material are removed prior to using the probe on a patient.

BRIEF DESCRIPTION OF THE DRAWINGS

FIG. 1 is an illustration, partly in section, of a hybrid-based probe of the type suitable for use with the sheaths of this invention.

FIG. 2 is a side view of the above type of probe.

FIG. 3 is an illustration in section of a side view of a sheath fitted to a hybrid-based probe.

DETAILED DESCRIPTION OF PREFERRED EMBODIMENTS

Figure 4:
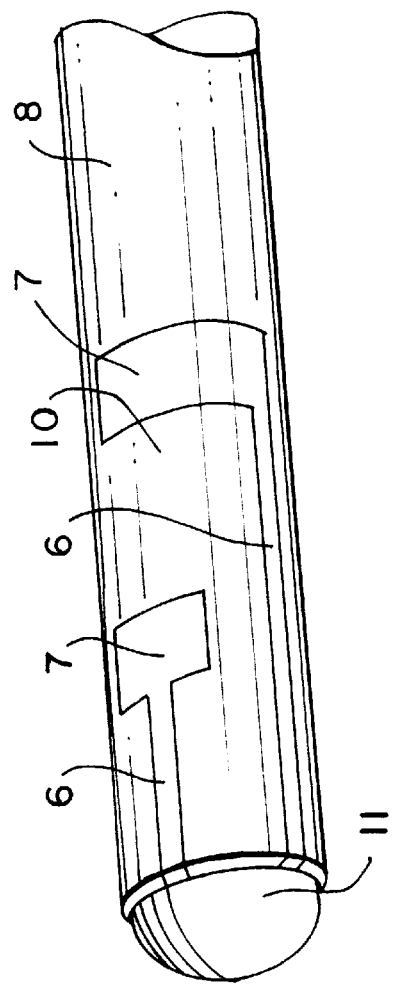
FIG. 4 is a perspective view of one embodiment of the invention.

The endocervical probe described above is a special case of a hybrid probe, which is described in detail in our copending application filed this same date entitled "Hybrid Probe For Tissue Type Recognition", the disclosure of which is incorporated herein by reference. As explained in that application, a hybrid probe is primarily distinguished by the avoidance of the use of optical fibers to convey illumination to and/or from the active portion of the probe. It is designed to examine areas of tissue having a diameter of the order of 2 mm, which requires that photodiode detectors be placed in close juxtaposition with light emitters yet optically isolated so that light signals do not pass directly from an emitter to a detector without intervention (i.e. backscattering) by the tissue under examination. This is accomplished in the hybrid probe by the use of metal barriers. The metal barriers also shield the detector circuitry from electrical interference carried by current pulses that must be applied to the LEDs to induce them to emit light to illuminate the portion of the tissue being tested. The metal barrier may be left floating or grounded, but can also serve an additional role as an electrode for making electrical measurements to replace or supplement the two or three noble metal electrodes adjacent to the hybrid circuit normally used for the electrical measurements to be made on the tissue.

In addition the hybrid structure has a preamplifier in close proximity to the photodiodes to amplify the small current from the photodiode detectors and feed it to the electronics in the handle of the probe and from there to the analysis circuitry.

Probes using optical fibers are temperature sensitive. This temperature sensitivity often occurs at bends in the fiber. It is often not practical to measure these temperatures so compensation is difficult to achieve. A change in temperature at the tip of the probe is likely to occur when the probe is brought into contact with the tissue of a warm blooded being. The hybrid probe overcomes the forms of temperature sensitivity arising from the fibers. The radiation output of LEDs is also temperature sensitive but for precise measurements can be compensated by using a characteristic of the LED to determine its own temperature. The bandgap potential of LEDs is a known function of temperature, allowing the temperature to be determined by applying a known current to the diode and measuring the potential across it. This can then be used to correct for the output of the LED using established equations thereby compensating for the changed radiation emission caused by temperature changes. Further details are provided in the accompanying application mentioned above.

An important requirement for the sheath is that it does not prevent the reading of the optical and electrical properties of the tissue being determined at effectively the same place. Where more than one electrode is employed, the electrodes should be essentially symmetrically positioned relative to the optical system.

The optical system for the probe typically employs hybrid systems that place the opto-electronics components in the part of the probe where the measurements are made. Other configurations of the probe optics are conceivable, but the invention will be described in terms of one based on hybrid technology.

FIG. 1 shows the type of probe which is suitable for use with this invention. It indicates the layout of the components both electrical and optical which take part in the measurements made by the probe. The body 1 of the probe is fitted with a PCB 2 on which are mounted the electrical and optical components. In this embodiment, four electrical connectors 3 connect the internal circuits of the probe to the outer surface of the probe. The electrical connectors 3 must make contact with mating parts on the sheath when it is fitted. The optical components (typically the three LED's 13 depicted in the figure and a photodetector 15) are mounted on each side of the barrier 9. FIG. 2 shows the same probe in plan and elevation.

Figure 5:
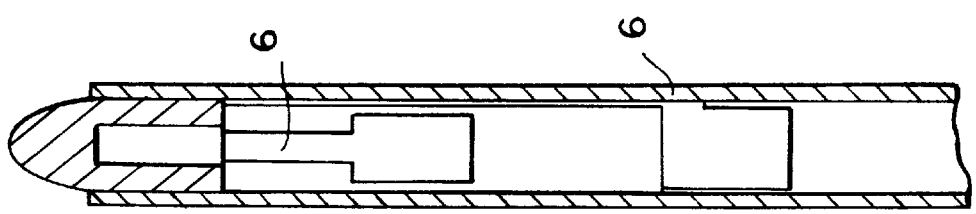
FIG. 5 is a cutaway view of the above embodiment rotated through 90 degrees.
Figure 6:
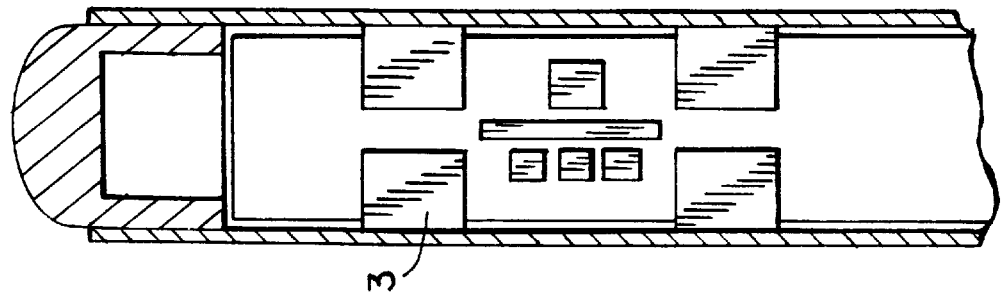
FIG. 6 shows the above embodiment fitted to a probe.

FIGS. 3 and 4 show the sheath of the present invention fitted to the probe. The body 8 of the sheath has attached to its surface electrodes 7 which may be put in place by suitable means such as vacuum evaporation or other plating means. These electrodes may be masked to a specific shape by coating them with a suitable lacquer. Extensions to the electrodes provide connectors 6 which extend to the tip of the sheath and continue around the tip edge and pass down the inside surface of the sheath 8. FIG. 5 shows how these connectors 6 appear on the inside of the sheath 8. Note that FIG. 5 has been rotated through 90 degrees relative to the previous illustrations. FIG. 6 shows the probe inserted in the sheath with the connectors 3 making contact the connectors 6. A cap 11 is fitted to the sheath to seal the front end.

Figure 7:
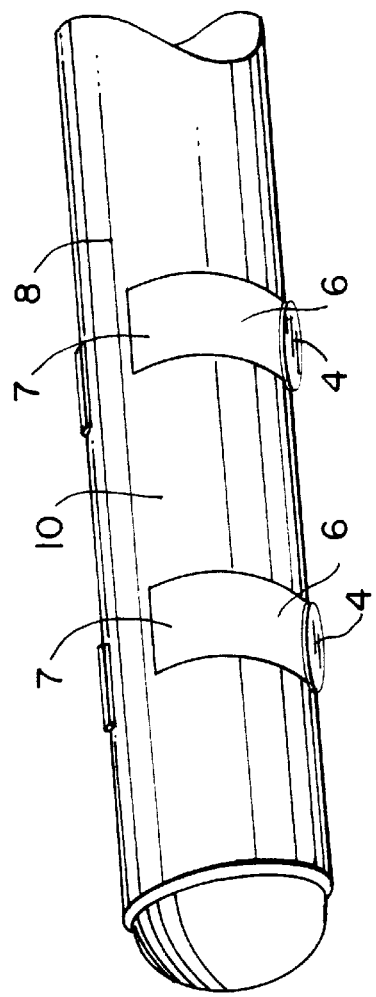
FIG. 7 is an illustration of another embodiment of the invention.
Figure 8:
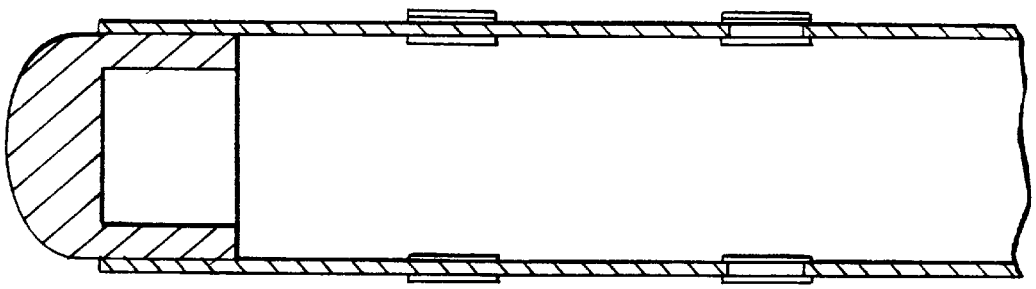
FIG. 8 is a cross section of the embodiment of FIG. 7.
Figure 9:
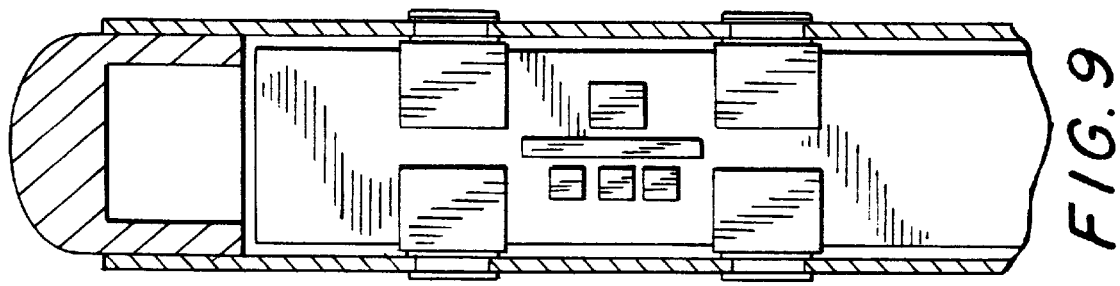
FIG. 9 depicts the embodiment of FIG. 7 fitted to a probe.

FIGS. 7, 8 and 9 show another embodiment of the invention wherein the connections from the inside of the sheath to the electrodes on the outside are provided by rivets 4. These rivets form contacts on the inside surface of the sheath which mate with the connectors 3 on the probe inside. It is important that a reliable seal be formed by the rivets so that no ingress of fluids can take place at these points.

An essential requirement of this configuration is that the window area 10 above the optical sections are in reliable contact with the body of the internal probe. Any space here would interfere with the reliability of the optical readings through internal reflections. A small amount of liquid can be included at this interface to ensure reliable optical coupling. The liquid may advantageously be thixotropic, such as an optically clear hand cleaning gel or a dentifrice gel, particularly a pediatric gel.

Orientation is also important. The electrodes must line up with their corresponding contacts on the probe body. To this end it is necessary to fit the probe body and the sheath with guides 17 and 19 that constrain the sheath to line up with the electrical contacts. Spiral grooves or various probe and sheath shapes such as the elliptical cross-section illustrated above can be employed for this purpose.

The thickness of the windows 10 is directly related to the width of the barrier 9 and the placement of the optoelectronic components in that section of the probe. The thickness of the window must be small enough that significant amounts of light from the emitters on one side of the barrier cannot reflect directly off the top surface of the window back to the detector on the other side of the barrier without passing via the tissue. Light which bypasses the tissue in this way will lower the discriminatory ability of the probe.

Provision needs to be made to ensure that the sheath is firmly secured in place after it has been fitted to the probe. This is conveniently achieved by arranging for a part of the sheath to be of smaller diameter than the probe and for a corresponding indentation to be present in the probe so that the sheath slips into that indentation thereby locking the sheath in place and providing a force which keeps the optical and electrical contacts secure while the probe is in use. A locking ring may also be employed. These locking devices are not illustrated.

A further aspect of the invention is the provision of a calibrator to check the performance of the sheathed probe prior to use. Calibrators are described in greater detail in a copending application filed this date entitled "Apparatus For Checking The Calibration Of Optical Probes", whose disclosure is incorporated herein by reference. As explained in that application, a probe may be calibrated by simply pressing the tip against a block of material of controlled characteristics. In this form of calibrator a transparent elastomer is used into which has been incorporated a light-scattering material. The light-scattering material can be any one of a number of whiteners such as titanium dioxide, barium sulphate, or magnesium oxide. The concentration of whitener is varied to suit the particular turbidity that is needed. The elastomer can be, for example, a polyurethane rubber or a silicone rubber.

Elastomer calibrators may be assembled on the tip with the other components of the sheath and is removed after calibrating the system and before the probe put into use.

Another form of calibrator comprises a turbid elastomer on the surface of which is placed a film of flexible polymer which is intended to simulate the structure of the material that is to be measured. The latter may for example be a layer of precancerous cells on cervical tissue. The layer of polymer film that is placed over the elastomer should have optical characteristics analogous to the material to be detected by the probe. In the case of cervical intra-epithelial neoplasia, the cervical tissue becomes covered with a layer of abnormal cells. A calibrator intended to check the performance of a device that is to detect this layer of cells may provide more reliable diagnoses if it is calibrated in an environment equivalent to that pertaining during the diagnostic probing, that is, by using a layered calibrator.

Figure 10:
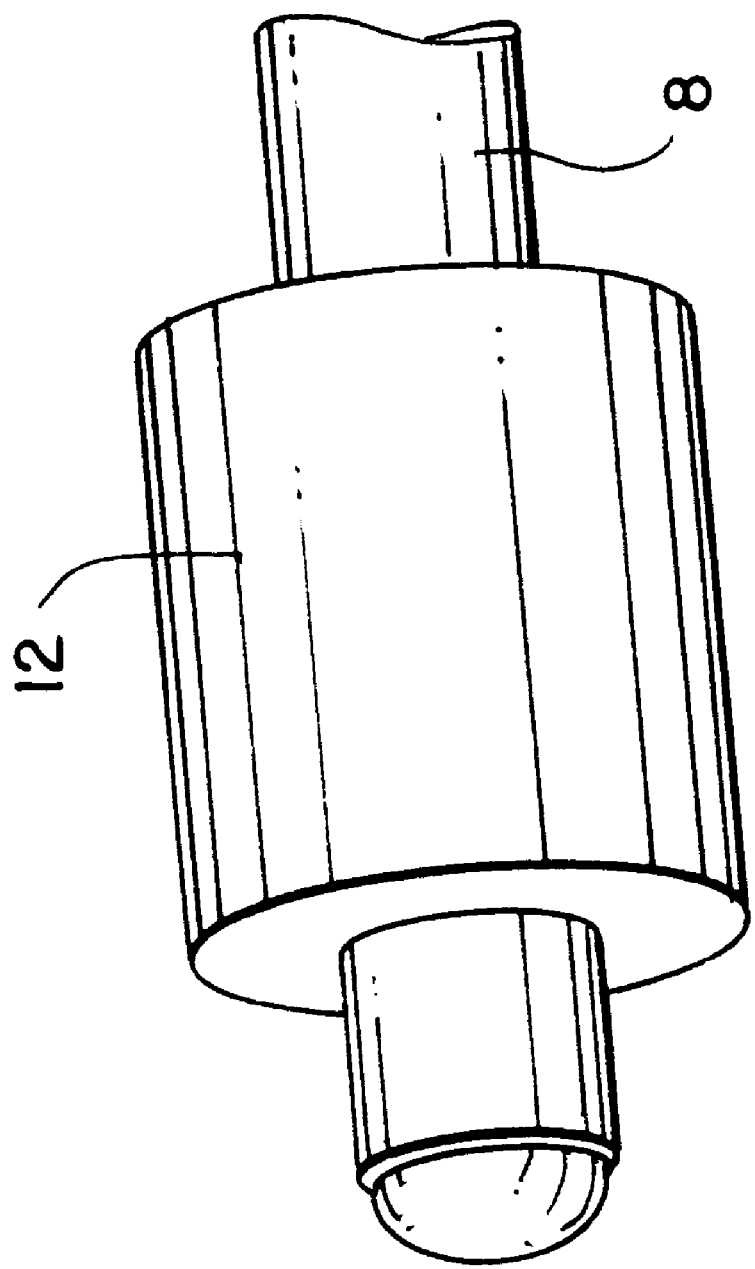
FIG. 10 depicts how a calibrator is fitted to the sheath.

FIG. 10 shows how a turbid calibrator 12 is fitted to the sheath. A liquid film may be included between the tip of the sheath 1 and the piece of turbid material to ensure that the optical coupling is reliable. Immediately prior to using the probe the operator advises the controller to perform a calibration check. The controller is typically programmed to refuse to function unless the calibration check is passed. The turbid calibrator 10 is then removed from the sheath exposing the face for application to the tissue to be examined. By performing these operations the danger of making erroneous measurements because the sheath is incorrectly fitted are avoided.

Although the invention has been described by giving preferred embodiments, the scope of the protection afforded by this patent is determined by the legitimate scope of the following claims.

What is claimed is:

1. A sheath having active regions for a side view probe used to examine the tissue of a patient, said sheath being removable from the probe and replaceable with another identical sheath upon said probe to prevent cross contamination between patients comprising, said probe having at least one optical radiation emitter, a plurality of optically transparent areas at the active regions of the sheath wherein optical radiation from said optical radiation emitter passes through the sheath in order to effectuate optical radiation from the probe onto said tissue, one or more electrodes adjacent to said optically transparent areas, said sheath having guide means that constrain the electrodes to align with corresponding electrical contacts on the probe, wherein electrical and optical measurements may be made simultaneously by the sheathed probe on area of tissue adjacent the sides of the probe.

2. The sheath for a side view probe of claim 1, wherein the probe comprises electrical contacts, said sheath is cylindrical and has a hoop tension, and said hoop tension forces a reliable electrical contact between electrodes on the active regions of the sheath and corresponding electrical contacts on the probe.

3. An apparatus as claimed in claim 1 wherein said sheath has thin transparent windows to pass radiation to and from optical elements of the side view probe.

4. An apparatus as claimed in claim 1 wherein said sheath has an inside wetted with a liquid that enhances optical coupling.

5. An apparatus as claimed in claim 4 wherein said optical liquid comprises mineral oil or glycerine.

6. An apparatus as claimed in claim 4 wherein said optical liquid is thixotropic.

7. An apparatus as claimed in claim 1 comprising a turbid material at the active areas which serves the purpose of checking the calibration of the probe and the precision of the optical coupling to the cover window and which can be removed prior to using the probe on a patient.

* * * * *